United States Patent [19]

Handley et al.

[11] Patent Number: 4,618,577
[45] Date of Patent: Oct. 21, 1986

[54] HUMAN-HUMAN HYBRIDOMA, CLNH5

[75] Inventors: Harold H. Handley, Cardiff-by-the-Sea; Mark C. Glassy, San Diego, both of Calif.; Yoshihide Hagiwara, Hyogo; Hideaki Hagiwara, Osaka, both of Japan

[73] Assignee: The Regents of The University of California, Berkeley, Calif.

[21] Appl. No.: 465,081

[22] Filed: Feb. 9, 1983

[51] Int. Cl.[4] .................. G01N 33/53; C12P 21/00; C12N 15/00; C12N 5/00; C12R 1/91
[52] U.S. Cl. ........................................ 435/7; 435/68; 435/172.2; 435/240; 435/948; 436/548; 436/813; 935/99; 935/110; 530/388
[58] Field of Search ............... 935/99, 106, 110; 435/7, 68, 240-244, 172.2, 948; 436/548, 813, 512; 260/112 B; 424/1, 9, 85

[56] References Cited

U.S. PATENT DOCUMENTS

| | | | |
|---|---|---|---|
| 3,654,090 | 4/1972 | Schuurs et al. | 435/7 |
| 3,927,193 | 12/1975 | Hansen et al. | 424/1.1 |
| 4,331,647 | 5/1982 | Goldenberg | 424/9 |
| 4,350,626 | 9/1982 | Masuho et al. | 435/172.2 |
| 4,359,457 | 11/1982 | Neville, Jr. et al. | 436/548 |
| 4,361,544 | 11/1982 | Goldenberg | 424/9 |
| 4,434,230 | 2/1984 | Ritts, Jr. | 435/240 |
| 4,443,427 | 4/1984 | Reinherz et al. | 435/172.2 |
| 4,451,570 | 5/1984 | Royston et al. | 435/241 |
| 4,454,106 | 6/1984 | Gansow et al. | 436/548 |

FOREIGN PATENT DOCUMENTS

| | | | |
|---|---|---|---|
| 2643207 | 3/1978 | Fed. Rep. of Germany | 436/512 |
| 8304313 | 8/1983 | PCT Int'l Appl. | 435/7 |
| 2086937 | 5/1982 | United Kingdom | 436/548 |

OTHER PUBLICATIONS

Schlom et al. (1980) Generation of Human Monoclonal Antibodies Reactive with Mammary Carcinoma Cells, Proc. Natl. Acad. Sci., 77(11): 6841-6845.

Primary Examiner—Esther M. Kepplinger
Assistant Examiner—Cynthia Lee Foulke
Attorney, Agent, or Firm—Leydig, Voit & Mayer

[57] ABSTRACT

Novel hybridomas, human monoclonal antibodies, and their uses are provided. Specifically CLNH5 is a human-human hybridoma which secretes IgM monoclonal antibodies specific for cervical of carcinomas. The monoclonal antibodies can find use in therapy and diagnosis, both in vitro and in vivo.

The hybridoma CLNH5 was deposited at the A.T.C.C. for patent purposes as defined in M.P.E.P. 608.01(p) on Jan. 28, 1983 and given A.T.C.C. Accession No. HB8206.

11 Claims, No Drawings

HUMAN-HUMAN HYBRIDOMA, CLNH5

BACKGROUND OF THE INVENTION

1. Field of the Invention

The mammalian immune system has a matchless ability to produce molecules with specificity and avidity for a particular spatial and polar structure, as may be found with sequences of amino acids and sugars. For a long period of time, one was dependent upon producing antibodies employing the immune system in vivo. The resulting polyclonal antibodies demonstrated high specificity for a specific antigen, but could not discriminate between various sites on the antigen and, furthermore, were a mixture of antibodies of varying specificity and avidity. Thus, one observed the averaging over the entire composition and not the properties of a specific antibody.

With the seminal discovery by Milstein and Kohler, one can now produce homogeneous compositions of antibodies by fusing a B-lymphocyte with a myeloma cell to produce a cell referred to as a hybridoma. For the most part, the use of this technology has been limited to mouse cells, where stable myeloma lines have served as fusion partners to provide stable hybridomas which can be produced with high efficiency and are capable of being maintained as productive entities over long periods of time. Higher organisms, particularly humans, have proven to be much more intractable in developing fusion partners and hybridomas. However, in 1980, the first human fusion partner was reported by Drs. Olsson and Kaplan and since that time, an additional few human fusion partners have been reported. Nevertheless, the preparation of hybridomas by human-human crosses has remained difficult due to problems of efficiency in fusion, culturing the cells, and maintaining their productive capabilities. However, because of the many advantages of having human hybridomas which product antibodies allogenic to a human host, particularly for in vivo applications, human hybridomas remain of great interest. In other instances, even with the difficulties encountered with human-human crosses, the human hybridoma may be preferable to a heterogeneic cross, where the resulting hybridoma may lose the genetic information for the monoclonal antibodies after a number of passages.

One of the areas of interest for the use of monoclonal antibodies is in diagnosing and treating cancer. Monoclonal antibodies for these purposes desirably are specific for a particular type of cancer or subset of cancers, rather than being specific for a particular host cancer cell. It is therefore desirable to develop monoclonal antibodies which can be used in the diagnosis and treatment of human cancers.

2. Description of the Prior Art

Nowinski et al., Science (1980) 210:537–539 describe human monoclonal antibodies against Forssman antigen. Croce et al., Nature (1980) 288:488–489 describe human hybridomas secreting antibodies to measles virus. Olsson and Kaplan, PNAS USA (1980) 77:5429–5431 describe human-human hybridomas producing monoclonal antibodies of predefined antigenic specificity as well as the fusion partner employed for production of the antibodies. See also copending application Ser. No. 247,652, filed Mar. 26, 1981, now U.S. Pat. No. 4,451,570.

Schlom, PNAS USA (1980) 77:6841–6845 describes monoclonal antibodies for breast cancer and Sikora, Brit. J. of Cancer (1981) 43:696 decribes separating in situ lymphocytes from a cancer providing antibodies specific for the cancer. In the Proceedings of the 15th Leukocyte Culture Conference, Parker and O'Brien, eds., Wiley Interscience, N.Y., Dec. 5-10, 1982, the subject hybridoma is described. This abstract is incorporated herein by reference.

SUMMARY OF THE INVENTION

Novel hybridomas based on the hybridoma CLNH5, novel monoclonal antibodies, and the use of the hybridomas and antibodies in the diagnosis and treatment of a subset of cancers is provided. Particularly, the subject antibodies appear to distinguish between cervical cancer and normal cells.

DESCRIPTION OF SPECIFIC EMBODIMENTS

The novel hybridoma CLNH5, hybridomas obtained from CLNH5, antibodies derived from such hybridomas, derivatives of such antibodies and the use of the antibodies and their derivatives for diagnosis and therapy are provided. CLNH5 is obtained by fusion between the fusion partner UC729-6 with lymphocytes from a lymph node of a patient having cervical cancer. UC729-6 is on deposit at the A.T.C.C. with Accession No. CRL 8061. UC729-6 was deposited for patent purposes in conjunction with the filing of application Ser. No. 247,652.

The lymphocytes employed for fusion were from a draining lymph node from the spinal area and peripheral blood lymphocytes from a patient having cervical carcinoma. The fusion is performed by combining the patient's lymph node cells with the fusion partner UC729-6 at a ratio of about 2:1 in a solution of about 35% polyethylene glycol in HEPES buffered RPMI 1640. The mixture of cells is then suspended in appropriate selective medium, particularly HAT medium containing about 10% fetal bovine serum, placed in walls at about $10^5$ cells per well and a sufficient time permitted for the cells to grow. The selective medium is replaced from time to time.

One of the wells from the above fusion provided a clone specifically reactive with the cervical cancer cells of the host patient and was designated CLNH5. This well provided human IgM monoclonal antibodies which react with antigen found on a variety of cervical carcinomas and other tumor cell lines, e.g. small cell carcinoma of the lung, but not with normal tissues and normal cell lines, which were tested.

The hybridomas and monoclonal antibodies can find use in a variety of ways, particularly as sources of genetic material, as reagents, and as precursors to products which find use as reagents.

The subject hybridomas may be used as a source of genetic material. For example, the subject hybridomas may be fused with other fusion partners to provide novel hybridomas having the same secretory capabilities as CLNH5 to provide antibodies having the same specificity. Such fusions may result in the production of antibodies having different heavy chains so as to provide the other classes or subclasses of antibodies, e.g. G.

The hybridoma may also be used as a source of DNA, which by hybrid DNA technology, the genes may be excised, introduced into an appropriate vector and used for transformation of a lymphoma for production of the mature antibodies.

The monoclonal antibodies can be used in a variety of ways, for both in vivo and in vitro diagnosis, as well as in therapy. For many applications, the antibodies will be labeled with a compound which imparts a desired property to the antibodies, such as providing a detectable signal, providing cytotoxicity, providing for localized electromagnetic radiation, or the like. Labels may include radionuclides, enzymes, fluorescers, toxins or the cytotoxic fragment of toxins, particles, metals, metalloids, etc. The antibodies may be incorporated in liposome membranes or modified with lipids, so as to be incorporated in such membranes. The antibodies by themselves or labeled, may be used in in vitro diagnosis for measuring the presence of antigens associated with cervical cancer, for in vivo diagnosis for introduction into a host, e.g. intravenously, in a physiologically acceptable carrier, e.g. PBS, or may be introduced for therapeutic purposes in the same manner. The amount of antibody employed will vary depending upon the particular application. Introduction of antibodies for diagnostic and therapeutic purposes has been extensively described in literature.

The entire antibody need not be used, for many applications only a fragment having intact variable regions will suffice. For example, Fab fragments, F(ab')$_2$ fragments, or Fv fragments may suffice.

The following examples are offered by way of illustration and not by way of limitation.

EXPERIMENTAL MATERIALS AND METHODS

Fusion and Selection of Hybridomas

Lymph nodes were teased with nugent forceps in RPMI 1640 media and isolated lymphocytes were cultured overnight at 37° C. and 5% CO$_2$ in RPMI 1640 with 10% fetal calf serum (FCS) and 2 mM L-glutamine. Lymphocytes were counted and mixed at a ratio of 2:1 with the human lymphoblastoid B cell line UC729-6 (Handley and Royston, 1982, in Hybridomas in Cancer Diagnosis and Treatment, eds. Mitchell and Oettgen, pp. 125-132, Raven Press, N.Y.), then fused with polyethylene glycol 1500 by a modification of the technique by Gefter et al., Somatic Cell Genetics (1977) 3:321-336. Fused cells were plated at 10$^5$ cells/well in a Costar 96 well microtiter plate with Hypoxanthine-Amethopterin-Thymidine (HAT) (Littlefield, Science (1964) 145:709-710) supplemented RPMI 1640 with 10% FCS and L-glutamine. Within 10-20 days, wells positive for hybridoma growth were assayed for human antibody production and their reactivity to a limited human cell panel by an enzyme immunoassay (EIA) determined. Wells positive for reactivity were cloned by limiting dilution without the use of feeder layers and expanded for further study.

Enzyme Immunoassay

Human monoclonal antibodies (MoAbs) and their reactivity to cells were detected by a modification by an EIA previously described (Handley et al., J. of *Immunologic Methods* (1982) 54:291-296, as modified by Glassy et al., J. *Immunologic Methods* (1983) 58:119). Briefly, 50 μl of either an affinity purified goat anti-human Ig or a 4×10$^6$ target cell/ml suspension was immobilized in triplicate wells of an immunofiltration manifold. The specially designed microtiter plate serves as both an incubation chamber and filtration manifold (VP no. 107; V and P Scientific, San Diego, CA). The bottom of each well contains a 0.6 mm hole over which is placed a 6 mm diameter glass fiber filter. Surface tension prevents fluid volumes less than 100 μl from draining through the hole until a vacuum is applied. When vacuum is applied, fluid is drawn through the filter and out the drain hole leaving particulate matter trapped on the filter. After washing 3 times with 0.3% gelatin in phosphate buffered saline, 50 μl of hybridoma supernatant were incubated 30 min at room temperature. Filters were then washed and incubated with 50 μl of a horseradish peroxidase conjugated goat anti-human Ig for an additional 30 min. Filters were washed again and incubated with 150 μl of a 400 μg/ml solution of ortho-phenylene diamine in citrate buffer. 100 μl of each well were then transferred to a new plate containing 50 μl of 2.5M H$_2$SO$_4$ and read on a Dynatek (Alexandria, VA) MR 580 micro-ELISA reader at 492 nm.

RESULTS

Table I outlines the results of the fusion attempting to produce anti-SCCC (squamous cell carcinoma of cervix) human MoAbs. The fusion producting CLNH5, a human-human hybridoma secreting a MoIgMk reactive with SCCC cell lines, generated 6 growth positive wells of 80 wells plated. Hybridoma CLNH5 was cloned (CLNH5.5) and expanded when found to react with the cervical carcinoma cell lines, CaSki and Hela.

TABLE 1

| | Generation and Identification of Human MoAbs. | | | | | |
|---|---|---|---|---|---|---|
| Lymph Node draining | # Lymphocytes fused | # Hybridomas generated | # Secreting Ig | | | # Human reactive |
| | | | M | G | A | |
| Cervical Carcinoma (SCCC) | 7.0 × 10$^6$ | 6 | 2 | 1 | 0 | 1 (CLNH5.5) |

The relative amounts of human MoAb bound to each of the cell lines listed was measured by EIA.

CLNH5.5 shows positive reactivity with carcinomas of the cervix (CaSki, Hela), lung (T293, Calu-1, and SK-MES-1), melanoma (SK-MEL-28), and prostate (LnCap). CLNH5.5 was negative for normal fibroblasts, T lymphocytes and peripheral blood lymphocytes. All other human MoAbs generated from this fusion were negative for those cell lines shown.

Hybridoma CLNH5 was deposited at the American Type Culture Collection, 12301 Parklawn Drive, Rockville, Md. 20852, on Jan. 29, 1983, and granted A.T.C.C. accession no. HB8206.

The subject monoclonal antibodies are useful for the diagnosing, imaging and potentially for treating cervical carcinoma as well as other reactive tumors. Because of the specificity of the monoclonal antibodies over a range of cervical carcinomas from different hosts, the subject antibodies can be used in different hosts, rather than solely with the host source of the antigen. Because the subject antibodies are human, they are less likely to produce a significant immune response when employed in in vivo diagnosis or therapy.

Although the foregoing invention has been described in some detail by way of illustration and example for purposes of clarity of understanding, it will be obvious that certain changes and modifications may be practiced within the scope of the appended claims.

What is claimed is:

1. A human hybridoma designated CLNH5 having A.T.C.C. Accession No. HB8206.

2. A hybridoma which expresses monoclonal antibodies having the same specificity as that of the monoclonal antibodies expressed by cell line CLNH5, A.T.C.C. Accession No. HB8206, which hybridoma is produced by fusion of CLNH5 with a fusion partner.

3. Monoclonal antibodies derived from hybridomas according to any of claims 1 or 2.

4. A monoclonal antibody fragment derived from a monoclonal antibody according to claim 3, having the binding specificity of the monoclonal antibody according to claim 3.

5. Monoclonal antibodies according to claim 4 labeled with a label capable of providing a detectable signal.

6. Monoclonal antibody fragments according to claim 4, labeled with a toxin.

7. Monoclonal antibodies according to claim 3 labeled with a label capable of providing a detectable signal.

8. Monoclonal antibodies according to claim 3 labeled with a toxin.

9. A method for determining the presence of a carcinoma which comprises:
   combining a sample from a host suspected of having a carcinoma cancer with monoclonal antibodies according to claim 3; and
   detecting the presence of the binding of said monoclonal antibodies to their homologous antigen.

10. A method according to claim 9, wherein said sample is host tissue.

11. A method according to claim 9, wherein said carcinoma is a cervical carcinoma.

* * * * *